US007180760B2

(12) United States Patent
Varrichio et al.

(10) Patent No.: US 7,180,760 B2
(45) Date of Patent: Feb. 20, 2007

(54) METHOD OF EFFICIENTLY PERFORMING FRACTIONAL VOLTAGE CONVERSION AND SYSTEM COMPRISING EFFICIENT FRACTIONAL VOLTAGE CONVERTER CIRCUITRY

(75) Inventors: Anthony J. Varrichio, Plano, TX (US); Benjamin A. Tranchina, Allen, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 0 days.

(21) Appl. No.: 11/105,332

(22) Filed: Apr. 12, 2005

(65) Prior Publication Data

US 2005/0259454 A1 Nov. 24, 2005

Related U.S. Application Data

(60) Provisional application No. 60/561,437, filed on Apr. 12, 2004.

(51) Int. Cl.
*H02M 3/18* (2006.01)
*H02M 7/00* (2006.01)

(52) U.S. Cl. .............................. 363/59; 363/60; 363/61

(58) Field of Classification Search .................. 363/59, 363/60, 61, 62
See application file for complete search history.

(56) References Cited

U.S. PATENT DOCUMENTS

| 4,578,772 | A | * | 3/1986 | Fujii | ........................... 708/844 |
|---|---|---|---|---|---|
| 5,414,614 | A | * | 5/1995 | Fette et al. | ..................... 363/59 |
| 5,680,300 | A | * | 10/1997 | Szepesi et al. | ................. 363/59 |
| 5,948,004 | A | | 9/1999 | Weijand et al. | |
| 6,021,056 | A | * | 2/2000 | Forbes et al. | .................. 363/60 |
| 6,169,673 | B1 | * | 1/2001 | McIntyre et al. | .............. 363/59 |
| 6,657,875 | B1 | | 12/2003 | Zeng et al. | |
| 2002/0068957 | A1 | | 6/2002 | Wolf et al. | |
| 2002/0101744 | A1 | | 8/2002 | DeMone | |
| 2003/0052729 | A1 | | 3/2003 | Hsu et al. | |

FOREIGN PATENT DOCUMENTS

DE    199 30 394 A1    1/2000

OTHER PUBLICATIONS

International Search Report issued for PCT/US2005/012254, dated Jul. 29, 2005.

\* cited by examiner

*Primary Examiner*—Bao Q. Vu
(74) *Attorney, Agent, or Firm*—Peter R. Lando; Christopher S. L. Crawford (57) ABSTRACT

Embodiments provide a capacitive voltage multiplier for efficiently producing multiples, including fractional multiples, of a power supply voltage use high, medium and low voltage field effect transistors for switching terminals of various capacitors into and out of connection with power supply or ground voltages in charge mode and with an output or other capacitor terminals for series connection in pump mode. A single non-overlapping clock is level-shifted up to the maximum voltage level required for switching to produce a desired output, then level shifted back down to lower levels with delay added as necessary according to embodiments.

18 Claims, 5 Drawing Sheets

METHOD OF EFFICIENTLY PERFORMING FRACTIONAL VOLTAGE CONVERSION AND SYSTEM COMPRISING EFFICIENT FRACTIONAL VOLTAGE CONVERTER CIRCUITRY

CROSS-REFERENCE TO RELATED APPLICATIONS

The present application claims priority to U.S. Provisional Patent Application Ser. No. 60/561,437, entitled "PULSE GENERATION CIRCUIT UNIVERSAL CUSTOM OUTPUT DRIVER," filed Apr. 12, 2004, the disclosure of which is hereby incorporated herein by reference. The present application is related to concurrently filed and commonly assigned U.S. patent application Ser. No. 11/105,191 entitled "SYSTEMS AND METHODS FOR PRECHARGING CIRCUITRY FOR PULSE GENERATION," U.S. patent application Ser. No. 11/105,186 entitled "SYSTEMS AND METHODS FOR PROVIDING AMPLITUDE SELECTION FOR PULSE GENERATION," U.S. patent application Ser. No. 11/105,188 entitled "ACTIVE DISCHARGE SYSTEMS AND METHODS," and U.S. patent application Ser. No. 11/105,190 entitled "VOLTAGE LIMITED SYSTEMS AND METHODS," the disclosures of which are hereby incorporated herein by reference.

TECHNICAL FIELD

The present invention is directed, in general, to providing selectable voltages and, more specifically, to providing voltage selection which includes fractional output of a supply voltage.

BACKGROUND OF THE INVENTION

In delivering constant current electrical stimulation pulses by an implantable pulse generator to electrodes implanted near a stimulation site, a voltage converter (multiplier) is desirable to produce driving voltages from a power supply voltage. Providing a variable voltage for use in the foregoing has typically involved the use of an inductive voltage converter or a capacitive voltage converter.

An inductive voltage converter requires the use of a coil for voltage conversion, which in turn necessitates the use of alternating current. The use of such coils with alternating current often results in inefficiencies with respect to power consumption associated with voltage conversion. For example, where a battery is used as a power source, complicated and inefficient switching regulator circuitry is typically required to convert the direct current from the battery to alternating current for voltage conversion. Moreover, an inductive up-converter may introduce too much electronic noise to permit wireless (e.g., radio frequency) communication between an implantable pulse generator and an external control unit. This may require the inductive up-converter to be shut down periodically in order to "listen" for communication signals, resulting in output voltage droop.

Capacitive voltage converters avoid problems resulting from electronic noise, but typically have been limited to providing voltage output in integer multiples of a supply voltage (e.g., $V_{Battery}$, $2V_{Battery}$, $3V_{Battery}$, etcetera). Such voltage converters only provide efficient operation at exact multiples of an input power supply voltage, with very poor efficiency at fractional multiples. In addition, depending on the design, capacitance for high voltage field effect transistors within the voltage multiplier may limit operating frequency. Such high voltage field effect transistors also consume substantial silicon area, while smaller field effect transistors lack acceptable reliability at high voltages that may be switched.

BRIEF SUMMARY OF THE INVENTION

To address the above-discussed deficiencies of the prior art, it is a primary object of embodiments of the present invention to provide a voltage converter adapted to supply voltage output in fractions of a supply voltage, such as that provided by a battery. Voltage converter configurations of embodiments of the invention use high, medium and low voltage components, such as field effect transistors, in generating a desired voltage, such as by switching terminals of various capacitors into and out of connection with power supply or ground voltages in charge mode and with an output or other capacitor terminals for series connection in pump mode, such that low voltage components see only low voltages, medium voltage components only see medium to low voltages, and high voltage components see only high to low voltages. Embodiments of the invention are provided for use in an implantable pulse generator, and may be used to control amplitude for a stimulation pulse delivered to electrodes implanted within a patient.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWING

For a more complete understanding of the present invention, reference is now made to the following descriptions taken in conjunction with the accompanying drawing, in which.

DETAILED DESCRIPTION OF THE INVENTION

FIGS. 1 through 7, discussed below, and the various embodiments used to describe the principles of the present invention in this patent document are by way of illustration only and should not be construed in any way to limit the scope of the invention. Those skilled in the art will understand that the principles of the present invention may be implemented in any suitably arranged device.

Before undertaking the detailed description below, it may be advantageous to set forth definitions of certain words or phrases used throughout this patent document: the terms "include" and "comprise," as well as derivatives thereof, mean inclusion without limitation; the term "or" is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; the terms "couple" and "connect" refer to any direct or indirect connection between two or more components, unless specifically noted that a direct coupling or direct connection is present; and the term "controller" means any device, system or part thereof that controls at least one operation, whether such a device is implemented in hardware, firmware, software or some combination of at least two of the same. It should be noted that the functionality associated with any particular controller might be centralized or distributed, whether locally or remotely. Definitions for certain words and phrases are provided throughout this patent document, and those of ordinary skill in the art will understand that such definitions apply in many, if not most, instances to prior as well as future uses of such defined words and phrases.

The general principles of the present invention are described with respect to an implantable pulse generator (IPG) for generating electrical stimulation for application to a desired area of a body, such as a spinal cord stimulation (SCS) system. It will be understood that the concepts of the present invention are not limited to an implantable pulse generator for use in an spinal cord stimulation system, but has broad applicability, including but not limited to different types of implantable devices such as spinal and neural stimulators and sensors, deep brain stimulators, cochlear stimulators, drug delivery systems, muscle tissue stimulators, and the like, including sensors and sensing systems. Moreover, the concepts of the present invention are not limited to use with respect to an IPG or any particular form of IPG. For example, embodiments of the present invention may be implemented with respect to a fully implantable pulse generator, a radio frequency pulse generator, an external pulse generator, a micro-implantable pulse generator, etcetera.

Figure 1:
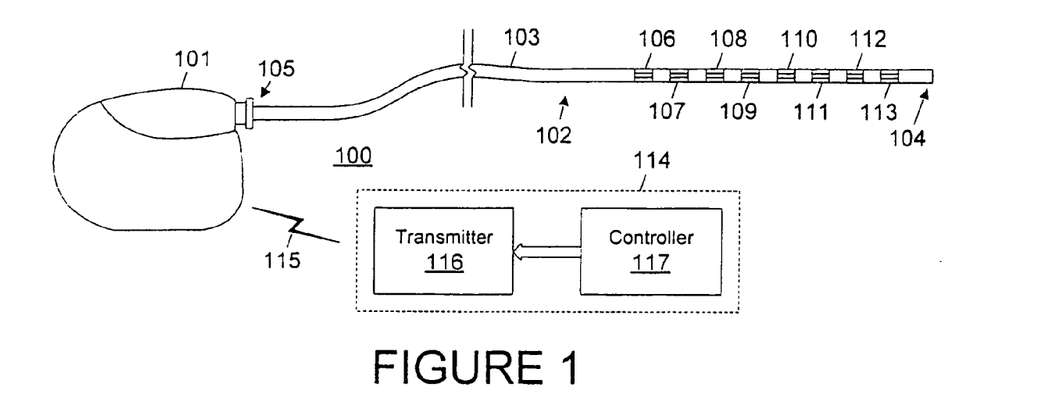
FIG. 1 depicts a stimulation system according to one embodiment of the present invention.

FIG. 1 depicts a stimulation system according to one embodiment of the present invention. The stimulation system 100 generates and applies a stimulus to a tissue or to a certain location of a body. In general terms, the system 100 includes an implantable pulse generator (IPG) 101 providing a stimulation or energy source and a lead 102 for application of the stimulus pulse(s).

Lead 102 includes a lead body 103 extending between a distal end 104 and a proximal end 105. Lead body 103 contains internal conductors, eight in the exemplary embodiment shown, extending a substantial distance of the length of lead 102 from the proximal end 105 towards the distal end 104, with the leads having lead connectors (not shown) at the proximal end 105 and terminating at exposed contact or ring stimulation electrodes 106–113 near the distal end 104. The conductors provide electrical connection from individual lead connectors to each of a corresponding one of electrodes 106–113. In the exemplary embodiment, the lead 102 is generally configured to transmit one or more electrical signals from implantable pulse generator 101 for application at, or proximate to, a spinal nerve or peripheral nerve, or other tissue via stimulation electrodes 106–113.

As will be appreciated, the connectors for electrodes 106–113 are situated within a receptacle of the implantable pulse generator 101 and are therefore not visible in FIG. 1. The connectors electrically connect electrodes 106–113 in lead 102 to individual outputs of a pulse generator circuit within the implantable pulse generator 101. The implantable pulse generator 101 generates and sends electrical signals via the lead 102 to the electrodes 106–113. The electrodes 106–113 are positioned at or proximate to one or more stimulation sites (not shown) within the body that is to receive electrical stimulation. Each stimulation site may be, for example, adjacent to one or more nerves in the central nervous system (e.g., spinal cord). The implantable pulse generator 101 is capable of controlling the electrical signals by varying signal parameters such as intensity, duration and/or frequency in response to control signals provided to the implantable pulse generator 101.

As will be appreciated, any number of conductors and corresponding stimulation electrodes may be utilized within lead 102, and lead 102 is shown with eight conductors/electrodes for purposes of illustration only. In addition, other types, configurations and shapes of stimulation electrodes (and lead connectors) known to those skilled in the art may be used. An optional lumen (not shown) may extend through the lead 102 and may be used for different purposes, including the delivery of chemicals or drugs.

Lead body 103 is a structure typically having a round cross-section, as in the exemplary embodiment, although the cross-section of the lead body 103 may be configured in any number of cross-sectional shapes appropriate for the specific application. Lead body 103 generally includes a lead body insulator configured to surround and insulate the conductors and present a biocompatible external surface to the body tissue, while leaving stimulation electrodes 106–113 exposed.

As shown in FIG. 1, the lead 102 in stimulation system 100 is coupled to the stimulation implantable pulse generator 101. In the exemplary embodiment, the implantable pulse generator 101 is either a self-contained implantable pulse generator (SCIPG) having an implanted power source such as a long-lasting or rechargeable battery or an externally-powered implantable pulse generator (EPIPG) receiving at least some of the required operating power from an external power transmitter, preferably in the form of a wireless signal, which may be radio frequency (RF), inductive, etc. As is known in the art, the implantable pulse generator 101 is capable of being implanted within the body (not shown) selected to receive electrical stimulation from the implantable pulse generator 101.

Stimulation system 100 also optionally includes an external programmer/controller 114 to program and/or control the implantable pulse generator 101 via a wireless communications link 115 between the implantable pulse generator 101 and the external programmer/controller 114. Implantable pulse generator 101 preferably includes an RF receiver (or transceiver) operative for wireless communications with an RF transmitter (or transceiver) 116 within programmer/controller 114. A controller 117 within programmer/controller 114 operates to control implantable pulse generator 101 via the wireless communications signals as described in further detail below.

When implantable pulse generator 101 is self-contained, the programmer/controller 114 may also provide power to the implantable pulse generator 101. Optionally, however, a separate power controller may be provided for charging the power source within implantable pulse generator 101. In some commercial embodiments, programmer/controller 114 is referred to as an external patient controller/programmer (EPP).

As shown in FIG. 1, lead 102 is coupled to implantable pulse generator 101, and is implanted together with the implantable pulse generator 101 with the electrodes 106–113 disposed proximate to the locations within a body that are to receive electrical stimulation. Implantable pulse generator 101 in turn receives communication/power signals at the RF receiver/transceiver therein via the wireless link 115 from programmer/controller 114 located outside the body to receive electrical stimulation.

Accordingly, a user of the stimulation system 100 may use the programmer/controller 114 to provide control signals for the operation of the implantable pulse generator 101 by operation of user controls (not shown) on programmer/controller 114 and functioning as inputs to controller 117. The controller 117 provides control signals to the transmitter 116, which transmits corresponding signals (and optionally power) to the receiver within the implantable pulse generator 101, which responsively varies the parameters of electrical signals transmitted through electrodes 106–113 to the stimulation site(s).

Figure 2:
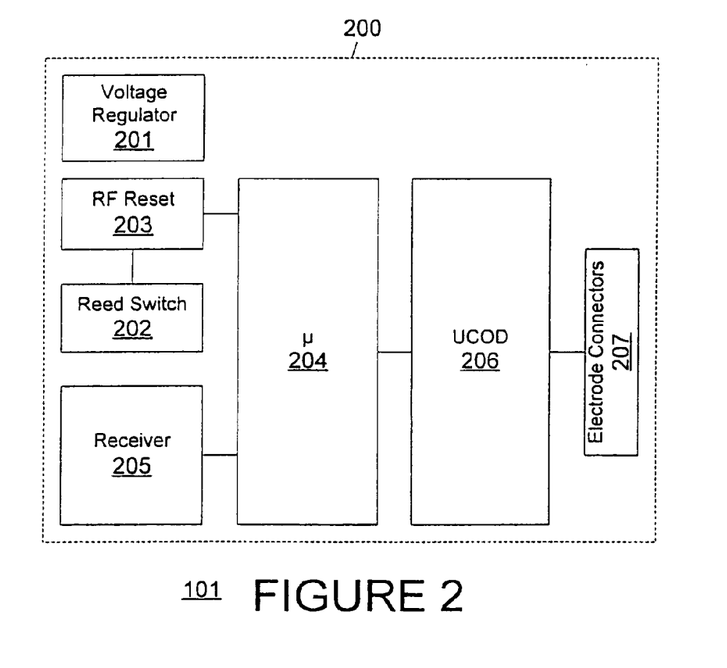
FIG. 2 is a high-level block diagram of a controller for an implantable pulse generator according to one embodiment of the present invention.

FIG. 2 is a high-level block diagram of a pulse generator controller within an implantable pulse generator according to one embodiment of the present invention. Pulse generator controller 200 is implemented by circuitry and/or software disposed within implantable pulse generator 101. In the exemplary embodiment, controller 200 includes a voltage regulator 201 and a reed switch 202 connected to an RF reset module 203, which is coupled in turn to a microprocessor (or microcontroller) 204. An RF receiver 205 is also connected to microprocessor 204, which is connected to the pulse generator circuit universal custom output driver (UCOD) 206. Universal custom output driver 206, preferably implemented as a single integrated circuit, is connected, in turn, to electrode connectors 207 receiving the connectors for lead 102.

Figure 3A:
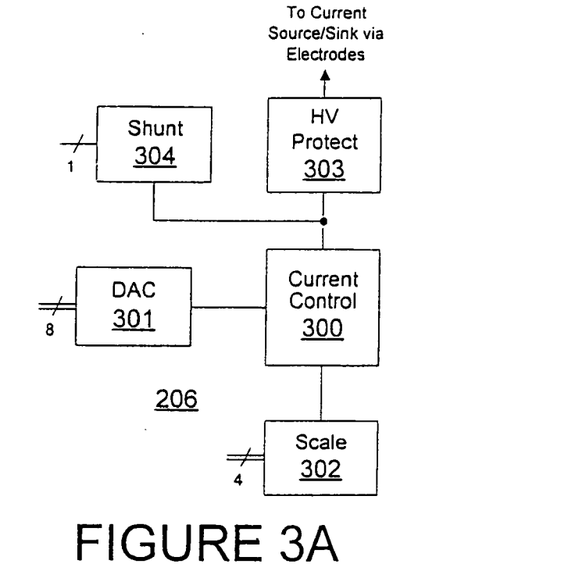
FIG. 3A is a block diagram for a portion of a pulse generator circuit including an output driver for an implantable pulse generator according to one embodiment of the present invention.

FIG. 3A is a block diagram for a portion of a pulse generator circuit including an output driver for an implantable pulse generator according to one embodiment of the present invention. Universal custom output driver 206 of the embodiment illustrated in FIG. 3A includes a current control mechanism 300 setting the current driven through the electrodes during delivery of an electrical stimulation pulse. A digital-to-analog converter (DAC) 301 and a scale circuit 302 current value set by current control 300 based on an eight-bit input signal and a four-bit input signal, respectively. In the exemplary embodiment, scale circuit 302 includes or is connected to a current source or sink.

Current control mechanism 300 is also connected via a high-voltage protection circuit 303 and the electrodes at which the electrical stimulation pulse is to be delivered to another current source or sink (that is, if scale circuit 302 includes or is connected to a current sink, the electrodes are connected to a current source and vice versa). In this manner, current control 300 forms part of a current path including the electrodes and the patient's body. A shunt circuit 304 is used to selectively direct current around the electrodes and patient to an alternate current sink or source, within or connected to shunt circuit 304, under control of a single input bit.

Figure 3B:
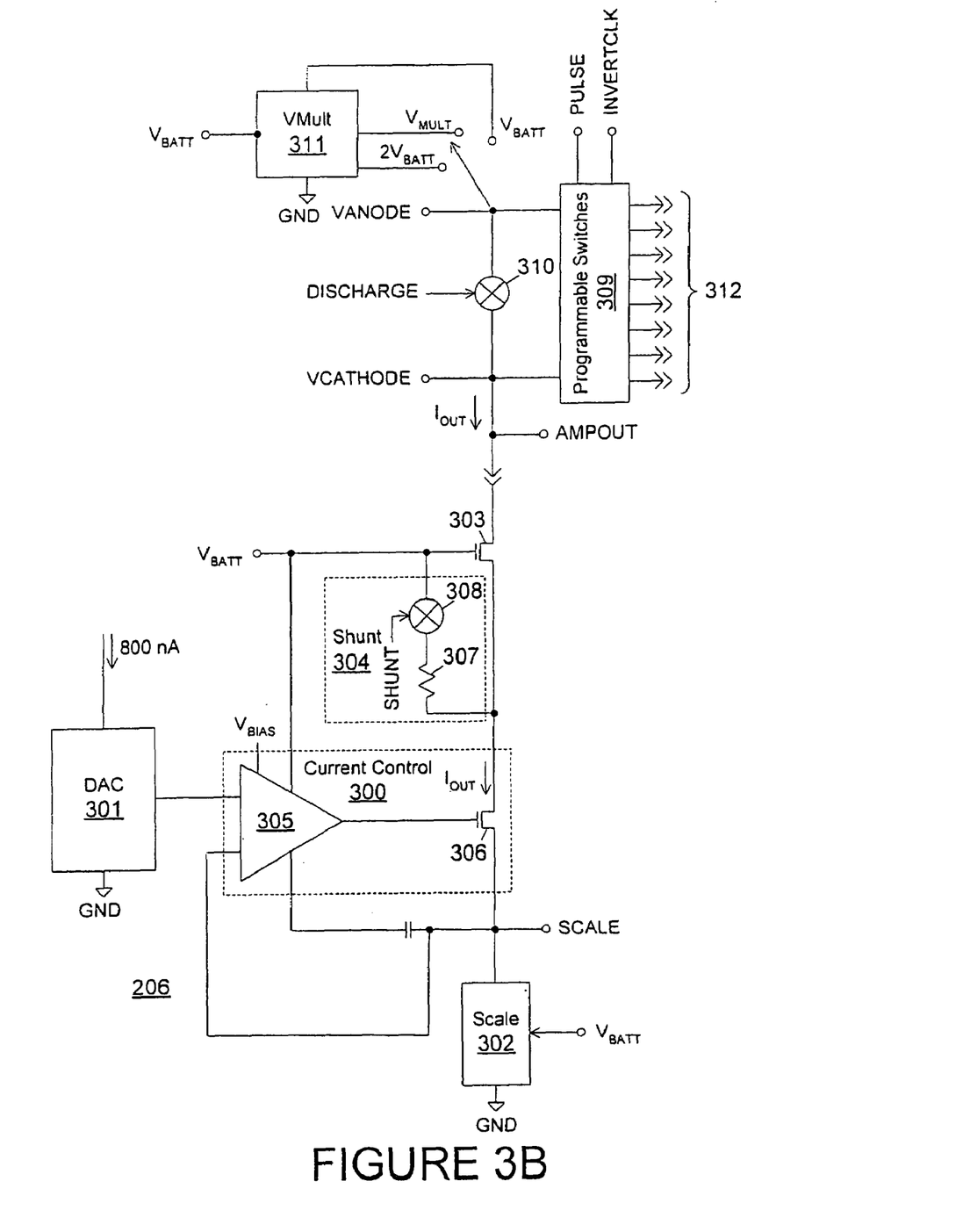
FIG. 3B is a simplified equivalent circuit diagram for a portion of a pulse generator circuit including an output driver for an implantable pulse generator according to one embodiment of the present invention.

FIG. 3B is a simplified equivalent circuit diagram for a portion of a pulse generator circuit including an output driver for an implantable pulse generator according to one embodiment of the present invention. In the equivalent circuit, the current control circuit 300 within universal custom output driver 206 includes an operational amplifier (op-amp) 305. The output of the operational amplifier 305 is connected to the gate of a field effect transistor (FET) 306. One terminal of transistor 306 is connected to a terminal of a high voltage protection source-follower configured transistor 303 and, through a shunt resistor 307 and a shunt switch 308 forming the shunt circuit 304, to the battery voltage $V_{BATT}$.

The other terminal of transistor 303 is connected to the AMPOUT signal, which in turn is coupled to the VCATHODE signal. The VCATHODE signal is connected by one of switches 309 to an electrode or optionally by switch 310 to a VANODE signal, corresponding to the voltage driven on the selected anode electrode. The VANODE signal is connected by one of programmable switches 309 to an electrode, and selectively to one of (a) the $V_{BATT}$ voltage, available on an output of the voltage multiplier 311, (b) the $V_{MULT}$ voltage generated by voltage multiplier 311 or (c) the $2V_{BATT}$ voltage generated by voltage multiplier 311.

The other terminal of transistor 306 (the one not connected to transistor 303) is connected to the SCALE input signal, to one input of operational amplifier 305, and to one terminal of scale circuit 302. Scale circuit 302 may be implemented, for example, by a digitally-controlled resistance that may be selectively varied. The variable output of scale circuit 302 is also connected to the same input of operational amplifier 305 as the terminal of transistor 306 and the SCALE input signal. The other terminal of scale circuit 302 is coupled to ground.

The variable output terminal of digital-to-analog converter 301 is connected to the other input of operational amplifier 305. The other terminal of digital-to-analog converter 301 is connected to a current mirror (not shown) transmitting a bias current $I_{BIAS}$ of approximately 800 nA through the digital-to-analog converter 301 to ground. The implementation of digital-to-analog converter 301 is preferably selected for monotonicity of the output function (e.g., a ladder resistor).

Current control 300 sets the amplitude of output current $I_{OUT}$ driven for the electrical stimulation pulse. Each of the outputs 312 for programmable switches 309 is connected through a capacitor (not shown) to one of the electrodes 106–113. Switches 309 programmably connect, with timing controlled by input signals PULSE and INVERTCLK, one or more of the electrodes 106–113 to the anode voltage VANODE and one or more of the electrodes 106–113 to the cathode voltage VCATHODE to deliver the electrical stimulation pulse to the desired location(s). In addition, each of outputs 312 may be selectively tri-stated (set to a high-impedance state), so that each electrode 106–113 may be connected as an anode, connected as a cathode, or tri-stated (off).

During operation, the universal custom output driver 206 stores switching patterns for controlling connection of switch outputs 312 within a memory (not shown). The switching patterns define parameters for electrical stimulation pulses, including the lead electrode 106–113 to be employed as anode and as cathode. For delivery of an electrical stimulation pulse according to embodiments of the invention, switches 309 connect at least one of the outputs 312 to the selected anode voltage VANODE, and at least one other of the outputs 312 to a cathode voltage VCATHODE (which is also the output voltage AMPOUT that may be employed for selective monitoring of any output pulse delivered). In this manner, an electrical pulse is selectively transmitted through selected one(s) of the electrodes 106–113 and returned through other selected one(s) of the electrodes 106–113 for delivery of that electrical pulse to the desired stimulation site(s) according to an embodiment.

The functionality of universal custom output driver 206 also includes inversion of the switching pattern(s) retrieved from the memory so that the previously selected anode electrode(s) becomes the cathode electrode(s) and the previously selected cathode electrode(s) becomes the anode electrode(s) (and all other electrodes remain unused). This functionality is employed for active discharge, as described in further detail below.

The universal custom output driver 206 also controls anode source voltage selection, selecting the anode voltage VANODE from one of twice a battery voltage $2V_{BATT}$, a voltage multiplier output voltage $V_{MULT}$, and the battery voltage $V_{BATT}$, all generated by capacitive voltage multiplier (VMult) 311 as described in further detail below.

Switches 309 are also employed to provide transition blanking, controlled one clock cycle blanking of the anode electrodes within the lead 102 upon a signal change for patient safety. Such blanking may be accomplished by selectively tri-stating the outputs 312 to provide blanking without altering the stored memory or register switching patterns. During delivery of an electrical stimulation pulse, switch 310, controlled by an input signal DISCHARGE, is normally open. Between pulses, switch 310 is closed to allow passive discharge of the capacitive connections between outputs 312 and corresponding electrodes 106–113.

Figure 4:
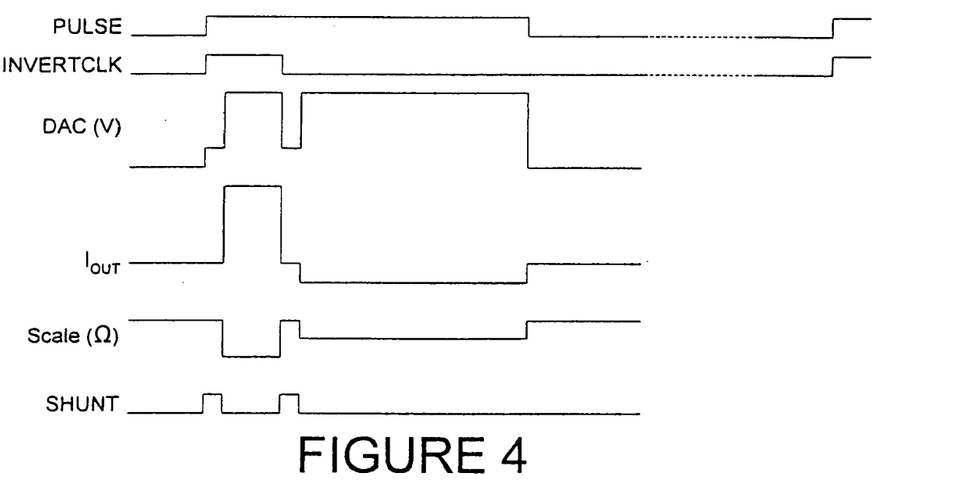
FIG. 4 is a timing diagram illustrating operation of a pulse generator circuit within an implantable pulse generator according to one embodiment of the present invention.

FIG. 4 is a timing diagram illustrating operation of a pulse generator circuit within an implantable pulse generator according to one embodiment of the present invention. The traces depicted illustrate, respectively from top to bottom, the PULSE signal, the INVERTCLK signal, the voltage at the variable output terminal of the digital-to-analog converter 301, the electrical stimulation constant current pulse $I_{OUT}$ delivered through the anode electrode, and the resistance at the variable output terminal of the scale circuit 302.

Amplifier Pre-charge

In implementing universal custom output driver 206 according to embodiments of the present invention, power consumption is balanced against slew rate. Operational amplifiers having a slew rate acceptable for high frequency operation (i.e., short electrical stimulation pulse duration) typically have high power consumption, an important consideration for battery life and/or the interval between required recharging cycles. Low power amplifiers, on the other hand, have a poor slew rate that can constrain the frequency or duration of electrical stimulation pulses, or simply provide poor stimulation performance.

The electrical stimulation pulse delivered to the patient through the anode and cathode electrodes is a programmable constant current pulse produced by forcing a known voltage across a very low sampling resistor that is electrically connected in series with the patient via source follower 303 through the selected cathode. Embodiments of the present invention enables use of a low power (and lower cost) implementation for amplifier used in delivering that pulse by providing a pre-charge period for each pulse. As illustrated in FIG. 4, the voltage at the variable output terminal of the digital-to-analog converter 301 is increased on the leading edge of the PULSE and INVERTCLK signals. This results in the output of operational amplifier 305 increasing to a predetermined voltage, preferably a voltage slightly above the voltage at which source follower transistor 306 begins conducting.

By pre-charging the internal electronics of the operational amplifier 305, which are biased using low internal voltages, and the output of operational amplifier 305 to an output voltage close to the threshold voltage at which transistor 306 begins conducting, the time required for the amplifier output voltage to be raised above that threshold voltage, turning transistor 306 on and initiating delivery of an electrical stimulation pulse through the anode and cathode electrodes, is reduced. Transistor 306 has a large width-to-length ratio to minimize resistance, which results in a high gate capacitance that can degrade slew rate. The constant current pulses delivered for electrical stimulation therefore have very fast rise times (slew rate).

To provide fast rise and fall times at low power consumption, an amplifier pre-charge period preceding the output pulse is employed, during which the amplifier is powered up but drives a low output current (about 100 microamperes) through the transistor 306 (by setting the scale circuit 302 to a high resistance value). Use of such a pre-charge period is facilitated according to embodiments since (a) a shunt path is provided, and (b) the amplifier output needs only to be operable for short, predictable periods of time, and may in fact be powered down (e.g., not a sleep mode) between pulses to reduce power consumption. The output current produced by pre-charging is shunted around the patient, with switch 308 closed by the SHUNT signal so that the delivered current passes through resistor 307. The output pulse to the patient starts immediately following the amplifier pre-charge period since the amplifier is already near the operating point (a change of only millivolts rather than volts is required).

The net pulse width of the output pulse delivered to the patient is the duration between the leading edge of the PULSE signal and the trailing edge of the INVERTCLK signal minus the amplifier pre-charge period. In the exemplary embodiment, the amplifier pre-charge period is programmable from 1–3 clock cycles in half-cycle steps. The reduction of the output pulse duration by the amplifier pre-charge period is automatic within universal custom output driver 206 of the illustrated embodiment, significantly reducing the burden on microcontroller or microprocessor 204.

In the illustrated embodiment of the present invention, transistor 306 at the output of operational amplifier 305, within the current sink path, is a field effect transistor (FET) rather than a bipolar junction transistor (BJT). This contributes to providing fast rise times following pre-charging, since a faster switching speed may be obtained.

To minimize wasted power during pre-charging, the resistance of scale circuit 302 is preferably set to the largest resistance value tolerable while still achieving acceptable rise time.

Constant Current Pulse with Scaling

The amplitude of the constant current output $I_{OUT}$ of the illustrated embodiment is controlled by the combination of digital-to-analog converter 301 and scale circuit 302. To deliver the electrical stimulation pulse at the end of the amplifier pre-charge period according to embodiments of the invention, the resistance of scale circuit 302 is reduced to a value corresponding to the selected, desired output current range, and switch 308 is concurrently opened. The digital-to-analog converter 301 of embodiments controls the precise output current within the selected range for the electrical stimulation pulse that is delivered. At the end of the output pulse, the amplifier is clamped and the resistance of scale circuit 302 is again raised to a higher value.

Rather than employing a fixed resistor within the current sink path and varying the voltage input to operational amplifier 305, or alternatively fixing the voltage input to the operational amplifier 305 and employing a variable resistance in the current sink path, embodiments of the present invention provide both a digitally-controlled variable voltage input to operational amplifier 305 and a variable resistance within the current sink path to control the output current for an electrical stimulation pulse. Such use of dual variable controls over the current amplitude is facilitated at least in part because digital-to-analog converter 301 is monotonic, as described above.

Use of dual variable controls allows the scale circuit 302 to be employed to set a range for the output current $I_{OUT}$, or as a coarse resolution control. Strictly by way of example, scale circuit 302 may be employed to select between one of the following ranges: 0–25.6 milliamperes (mA), 0–12.8 mA, 0–6.4 mA or 0–1.6 mA.

Digital-to-analog converter 301 is then employed to select a particular (stepped) output current $I_{OUT}$ within the selected range, or as a fine resolution control. In the exemplary embodiment, the resolution depends on the number of step increments provided by digital-to-analog converter 301 and the range selected by scale circuit 302. That is, scale circuit 302 of embodiments provides ratiometric output current accuracy through resistance adjustment while digital-to-analog converter 301 provides monotonic output current accuracy through voltage adjustment. For instance, using the above-described exemplary ranges, a digital-to-analog converter 301 capable of operation in 256 increments would have a resolution of 100 microamperes (µA) for the largest range of 0–25.6 mA, a resolution of 50 µA for the second-largest range of 0–12.8 mA, a resolution of 25 µA for the next-to-smallest range of 0–6.4 mA, and a resolution of 6.25 µA for the smallest range of 0–1.6 mA.

In operation according to embodiments of the invention, scale circuit 302 is programmably controlled to automatically select the smallest range permitting delivery of the target output current amplitude. For example, if an output current amplitude of 6.2 mA is desired for an electrical stimulation pulse, scale circuit 302 of an embodiment will automatically be set for the above-described exemplary range of 0–6.4 mA, rather than the higher ranges of 0–12.8 mA or 0–25.6 mA. Selection of the smallest range including the desired stimulation pulse amplitude both reduces power dissipation by the output driver to conserve power and allows maximum (fine) stimulation pulse amplitude adjustment resolution to be used in any adjustment by the patient.

A benefit of the coarse and fine resolution approach described above is that the finer resolution inherently achieved at lower output current ranges is better suited for patient adjustment. If a large amplitude current pulse is required for stimulation (say, 20 mA), coarse adjustment (e.g., in increments of 100 µA) will be acceptable to the patient, who might not perceive any difference if finer resolution adjustment (e.g., in increments of 6.25 µA) were provided at that output current pulse amplitude level.

In embodiments of the present invention, scale circuit 302 serves three functions: selection of the output current $I_{OUT}$ or range during delivery of the electrical stimulation pulse; scaling of the output current $I_{OUT}$ by 1:1, 1:2 or 1:4 during the active discharge (described below); and scaling of the output current $I_{OUT}$ to a low level during the amplifier pre-charge period, as described above. From the above, it should be appreciated that the use of digital-to-analog converter 301 and scale circuit 302 of embodiments of the present invention provides control with respect to the output pulse current for providing scaling (e.g., magnitude selection), ramping (e.g., selection of incrementally larger or smaller magnitudes within a series of pulses), stimulation pulse/active discharge pulse ratio selection (e.g., 1:1, 1:2, or 1:4 ratio selection), and pulse wave shaping (e.g., selection of different magnitudes within a pulse to provide a stepped pulse etcetera).

In addition to contributing to providing fast rise times through pre-charging, the use of field effect transistor 306, digital-to-analog converter 301 and scale circuit 302 in combination with operational amplifier 305 in the present invention improves relative accuracy (versus less-important absolute accuracy) during scaling of the output pulse current. Use of field effect transistor 306 also facilitates direct error measurement based on the gate voltage, and results in less overhead voltage being "thrown away." Use of digital-to-analog converter 301 and scale circuit 302 further facilitates scaling for active discharge, described below.

Patient Shunt

In addition to enabling pre-charging of operational amplifier 305, the shunt path provided by resistance 307 and switch 308, under the control of SHUNT signal, improves reliability of operation and patient safety by preventing delivery of leakage current to the stimulation site between pulses. Optionally an overvoltage or other exceptional condition may also close switch 308 to make the shunt path available in lieu of driving current through the patient.

Switch 310, around switches 309 and electrode outputs 312, could optionally be switched in conjunction with switch 308, providing a low-resistance path around the lead 102 to minimize any current flowing through the electrodes should a current pulse be inadvertently delivered.

Active Discharge Control

Figure 5:
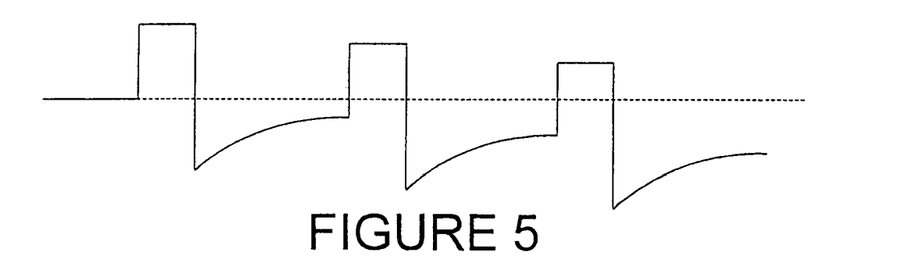
FIG. 5 illustrates possible voltage accumulation at capacitive connections between the output switches of a pulse generator circuit and lead electrodes during stimulation pulse delivery if only passive discharge is employed.

As previously described, the electrodes 106–113 within lead 102 are connected to switches 309 by capacitors (not shown). Because field effect transistor 306 is employed within the current sink path of the illustrated embodiment rather than a bipolar junction transistor (for which a base current is required in order to have collector current), simply removing power does not ensure that passive discharge (capacitive bleed-off) does not include delivery of an inadvertent and potentially stimulating current to the electrodes. In addition, where high pulse rates are used—e.g., occurring at frequencies above approximately 250 Hertz (Hz)—passive discharge may not fully discharge the capacitors and may result in charge accumulation, as illustrated in FIG. 5.

In embodiments of the present invention, following delivery of an electrical stimulation current pulse, a signal having the opposite polarity is driven to discharge the capacitors, as depicted in FIG. 4. After a one clock cycle blanking period following the trailing edge of the INVERTCLK signal, in the illustrated embodiment, a non-stimulating current (stimulation is direction-specific) is driven in the opposite direction through the electrodes used to delivery the stimulation pulse. During delivery of that non-stimulating pulse, switches 309 reverse the anode and cathode electrodes that were employed to deliver the stimulation pulse. That is, if electrode 112 was the anode and electrode 111 was the cathode for the stimulation pulse, electrode 111 will be the anode and electrode 112 will be the cathode for the subsequent active discharge pulse.

In addition, despite the direction-specific nature of stimulation pulses, inadvertent stimulation may be further avoided by driving the (negative) active discharge pulse with 1/nth of the magnitude and n times the duration of the stimulation pulse. That is, the active discharge pulse may have one-fourth the current amplitude of the electrical stimulation pulse just delivered, but four times the duration, resulting in substantially the same net charge or current flow. The capacitive connections between the pulse generator circuit and the electrodes may thus be substantially fully discharged (although nominal remaining charge or reverse charge is acceptable, and may be depleted by passive discharge between pulses). The scale circuit 302 provides the necessary scaling of the current magnitude, while active discharge timing control to the operational amplifier 305 provide scaling of the active discharge pulse width (duration). In the present invention, the current and pulse width scaling is programmable to 1:1, 2:1 or 4:1 (i.e., n=1, n=2 or n=4).

By delivering consecutive pulses of opposite polarity but equal energy, the net charge remaining on the output capacitors connecting switches 309 to electrodes 106–113 is reduced to near zero. Passive discharge, facilitated by switch 310, should easily dissipate any remaining charge accumulation before the next stimulation pulse is initiated.

Those skilled in the art will note that active discharge could as much as double (200%) the power consumed during delivery of stimulation pulses, shortening the battery life or recharge cycle interval. In the present invention, however, both the anode voltage and the pulse current can be controlled simultaneously (or individually), with the pulse current controlled by the variable output of digital-to-analog converter 301, the variable resistance of scale circuit 302, or a combination of the two. Simultaneous selection of (a) a different anode source voltage than used for delivery of the stimulation pulse, and (b) a lower variable output value of scale circuit 302 may reduce overall power consumption for active discharge, taken together with stimulation, from 200% to 125%. That is, the same current is driven between the electrodes, but at less power since the resistance (provided by scale circuit 302) within the sink path is reduced. Alternatively, power consumption may be somewhat reduced by adjustment of only one of the anode source voltage and the variable output of digital-to-analog converter 301 alone, with a corresponding adjustment of the variable output for scale circuit 302. In either case, however, active discharge is asymmetrical and low power relative to simple use of balanced pulses driven for identical durations and with identical current amplitude, without variation of the driving voltage and the sink path resistance.

Since the combined stimulation and active discharge pulses have a total duration of up to five times the desired stimulation pulse width, a malfunction resulting in the stimulation and active discharge pulses being delivered in the same direction (rather than opposite directions) at the stimulation site could present a hazard to the patient. For this reason, output switches 309 are preferably monitored to confirm polarity change and mitigate the potential hazard.

High Efficiency Capacitive Voltage Multiplier

Voltage multiplier 311 depicted in FIG. 3B receives as an input at least the battery voltage signal $V_{BATT}$, and produces and outputs a set of voltages selected from $\frac{1}{2}V_{BATT}$, $V_{BATT}$, $1\frac{1}{2}V_{BATT}$, $2V_{BATT}$, $2\frac{1}{2}V_{BATT}$, $3V_{BATT}$ and $4V_{BATT}$, or alternatively has the outputs shut off. Accordingly, voltage multiplier 311 of the illustrated embodiment provides a fractional voltage converter. The particular set of voltages from those listed that are produced and output by voltage multiplier 311 is programmably controlled, but always includes $V_{BATT}$ and $2V_{BATT}$ in the exemplary embodiment. Moreover, the particular voltages provided by a voltage multiplier implemented according to embodiments of the present invention are not limited to those set forth above. For example, voltage multiplier 311 may receive as an input at least the battery voltage signal $V_{BATT}$, and produces and outputs a set of voltages selected from $\frac{1}{4}V_{BATT}$, $\frac{1}{2}V_{BATT}$, $\frac{3}{4}V_{BATT}$, $V_{BATT}$, $1\frac{1}{4}V_{BATT}$, $1\frac{1}{2}V_{BATT}$, $1\frac{3}{4}V_{BATT}$, $2V_{BATT}$, $2\frac{1}{4}V_{BATT}$, $2\frac{3}{4}V_{BATT}$, $3V_{BATT}$, $3\frac{1}{4}V_{BATT}$, $3\frac{1}{2}V_{BATT}$, and $3\frac{3}{4}V_{BATT}$, or off.

Figure 6A:
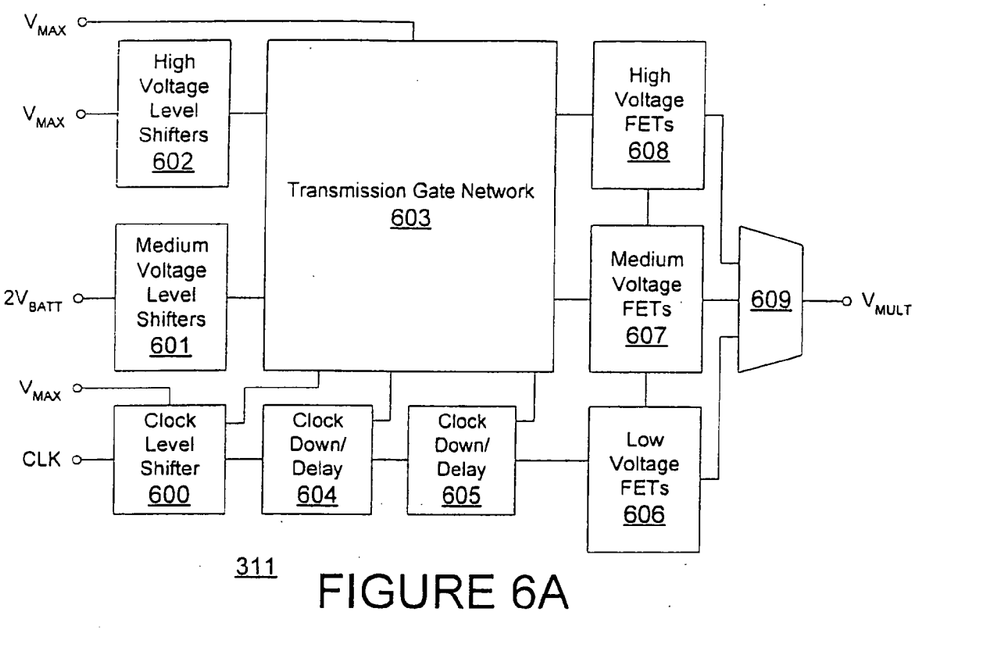
FIGS. 6A and 6B are a block diagram and a simplified equivalent circuit diagram of portions of a high efficiency capacitive voltage multiplier that may be employed for the output driver of an implantable pulse generator according to one embodiment of the present invention.
Figure 6B:
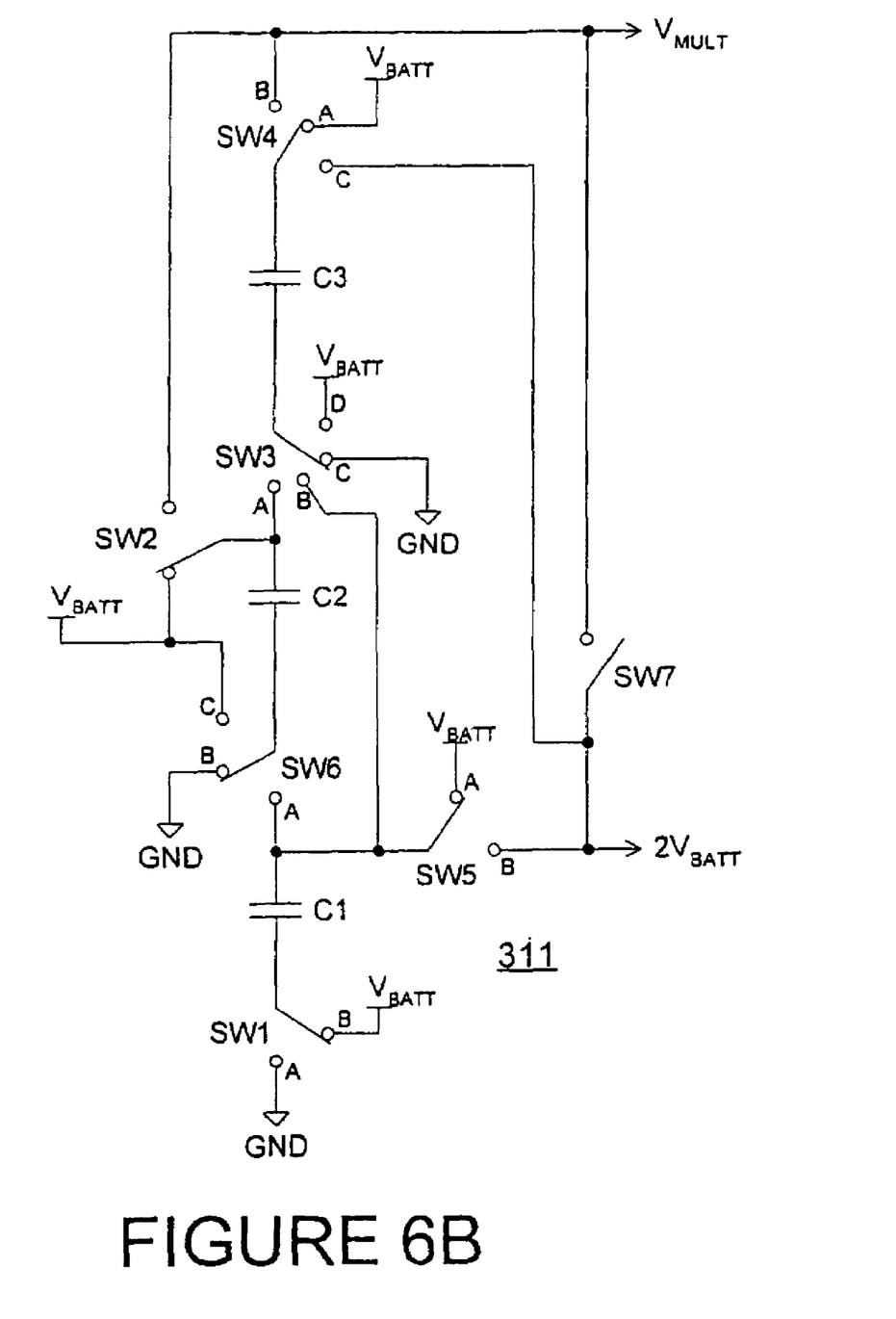

FIGS. 6A and 6B are a block diagram and a simplified equivalent circuit diagram of portions of a high efficiency capacitive fractional voltage multiplier that may be employed for the output driver of an implantable pulse generator according to one embodiment of the present invention. As depicted in FIG. 6A, voltage multiplier 311 includes a clock level shifter 600, medium voltage (up) level shifter(s) 601, high voltage (up) level shifters 602, a transmission gate network 603, clock down voltage level shifter/delay units 604 and 605, low, medium and high voltage level switching field effect transistors 606, 607 and 608, and a multiplexer 609.

To provide the different anode voltages (e.g., $\frac{1}{2}V_{BATT}$, $V_{BATT}$, $1\frac{1}{2}V_{BATT}$, $2V_{BATT}$, $2\frac{1}{2}V_{BATT}$, $3V_{BATT}$ and/or $4V_{BATT}$) employed for both precise current magnitude control and reduced power active discharge, a switch capacitive voltage multiplier 311 is implemented by a charge multiplier (charge pump) using level shifters and field effect transistors driven by a non-overlapping clock. Conventional techniques for implementing a charge multiplier using level shifters may be employed, using an array of selectable low impedance switches to charge and discharge a set of pump capacitors into larger output capacitors to produce the desired output voltage from the voltage multiplier (VMult) 311.

For reliability, high-voltage field effect transistors are generally preferred, for example, for output switching (or in level shifting or connection by the transmission gate network in the implementation of the present invention) of the higher voltages produced by the voltage multiplier. Such high-voltage field effect transistors consume a much larger area (three to five times as much) than low-voltage field effect transistors having similar conductivity, and are substantially less power efficient.

In addition, capacitive multipliers exhibit acceptable efficiency in generating exact multiples of an input voltage, but poor efficiency in between such voltage points. It would be useful to provide fractional multiples of the input voltage at an output (i.e., $\frac{1}{2}V_{BATT}$, $1\frac{1}{2}V_{BATT}$, and/or $2\frac{1}{2}V_{BATT}$).

Accordingly, in embodiments of the present invention, a combination of high-voltage, medium-voltage, and low-voltage field effect transistors 606–608 are employed in different portions of the voltage multiplier 311 depending on the voltage level produced. High-voltage field effect transistors are employed for level shifting, in the transmission gate network, and for output switching of, for example, $4V_{BATT}$ voltages. Medium-voltage field effect transistors are employed for level shifting, in the transmission gate network, and for output switching of $2V_{BATT}$ voltages. Low-voltage field effect transistors are employed in the transmission gate network and for output switching of $V_{BATT}$ voltages.

For the higher output voltages (e.g., $3V_{BATT}$ or $4V_{BATT}$), the output switches 607–608 of the illustrated embodiment are clocked by a higher voltage signal consistent with the output voltage being switched. Accordingly, the received clock signal is level shifted up to the appropriate voltage level (e.g., from 2.2 V up to 14 V). Use of three separate level shifters would unduly complicate clock synchronization. Accordingly, in embodiments of the present invention, all clocks instead are synchronized through a single up level shifter 600, which shifts the clock signal up to the maximum voltage level. The clock signal is then level shifted back down as needed in level shifters/delay units 604–605. Since high-voltage field effect transistors require longer switching speeds, use of high-voltage field effect transistors to level shift up to the highest voltage (and partially back down, as appropriate), and medium-voltage and low-voltage field effect transistors in level shifting back down to the medium and low voltages, reduces the complexity of synchronization, requiring that less delay be introduced in level shifters/delay units 604–605.

The clock signals are passed through the transmission gate network, but preferably only to those switching devices 607–608 necessary to output the appropriate voltage transmitted by level shifters 601–602. The transmission gates within network 603 are preferably pull-up and/or pull-down transmission gates, such that when a transmission gate is off, the corresponding switching device within field effect transistors 607–608 is also off. Since source-drain connections are used to pass voltages through the transmission gate network 603, (gate) capacitance effects are reduced, lowering the power consumed by voltage multiplier 311.

The minimum number of high-voltage field effect transistors possible are preferably employed to level shift up to the maximum voltage. Medium-voltage and low-voltage field effect transistors are then used to truncate down to other desired output voltages (less than the maximum). Power consumption from charging and discharging the gates of the medium-voltage and low-voltage field effect transistors is thereby reduced, since level shifting down requires less through-current than level shifting up. In addition, this configuration of high-voltage, medium-voltage and low-voltage field effect transistors reduces control clock speed requirements.

Use of high-voltage field effect transistors to level shift up to the maximum then truncating down using medium-voltage and low-voltage field effect transistors suggests the use of a non-overlapping clock at the highest voltage, and to maintain synchronous timing through the network. However, using a non-overlapping clock at each stage also minimizes through-current and switched capacitance.

FIG. 6B is a simplified equivalent circuit diagram illustrating generation of different voltages by voltage multiplier 311. Switches SW1–SW7 switch the three capacitors C1–C3, to charge one or more of the capacitors in charge mode and to output a desired voltage in pump mode. Switch SW1 switches a lower terminal of capacitor C1 between either the battery voltage $V_{BATT}$ or the ground voltage GND. Switch SW2 connects the upper terminal of capacitor C2 (and, depending on the state of switch SW3, possibly also the lower terminal of capacitor C3) to either the battery voltage $V_{BATT}$ or the output voltage terminal $V_{MULT}$.

Switch SW3 connects the lower terminal of capacitor C3 to either the battery voltage $V_{BATT}$, the ground voltage GND, the upper terminal of capacitor C1 (and, depending on the state of switch SW5, possibly also the doubled battery voltage output terminal 2 $V_{BATT}$), or the upper terminal of capacitor C2. Switch SW4 connects the upper terminal of capacitor C3 to either the battery voltage $V_{BATT}$, the output voltage terminal $V_{MULT}$, or the doubled battery voltage output terminal 2 $V_{BATT}$.

Switch SW5 connects the upper terminal of capacitor C1 (and, depending on the states of switches SW3 and SW6, possibly also the lower terminals of capacitors C2 and/or C3) to either the battery voltage $V_{BATT}$ or to the doubled battery voltage output terminal 2 $V_{BATT}$. Switch SW6 connects the lower terminal of capacitor C2 to either the battery voltage $V_{BATT}$, the ground voltage GND, or the upper terminal of capacitor C1. Switch SW7 selectively connects the output voltage terminal $V_{MULT}$ to the doubled battery voltage output terminal 2 $V_{BATT}$.

In accordance with the known art, switches SW1–SW7 are controlled for charge doubling. For instance, the voltage 2 $V_{BATT}$ may be generated by connecting the lower terminal of capacitor C1 to the ground voltage GND and the upper terminal of capacitor C1 to the batter voltage $V_{BATT}$ during charge mode, then connecting the lower terminal of capacitor C1 to the battery voltage $V_{BATT}$ and the upper terminal of capacitor C1 to the doubled battery voltage output terminal 2 $V_{BATT}$ in pump mode. Similarly, charging capacitors C1–C3 to the battery voltage $V_{BATT}$ in charge mode, then connecting the capacitors C1–C3 in series, with the lower terminal of capacitor C1 connected to the battery voltage $V_{BATT}$ and the upper terminal of capacitor C3 to the output voltage terminal $V_{MULT}$ to produce the voltage 4 $V_{BATT}$ at the output voltage terminal $V_{MULT}$.

In addition, voltage multiplier 311 of the illustrated embodiment of the present invention is also capable of producing half-step increments for the output voltage. For instance, capacitors C2–C3 may be connected in series and jointly charged to the battery voltage $V_{BATT}$ in charge mode, then connected at the common point (the upper terminal of capacitor C2 and the lower terminal of capacitor C3) to the output voltage terminal $V_{MULT}$ to produce the voltage $\frac{1}{2}$ $V_{BATT}$. While not implemented by the exemplary embodiment of voltage multiplier 311, the principle described above for generating half-step increments of the battery voltage $V_{BATT}$ could be readily extended to efficiently generate other fractional multiples of the battery voltage (e.g., $\frac{1}{3}$ $V_{BATT}$, $\frac{1}{4}$ $V_{BATT}$, $\frac{2}{3}$ $V_{BATT}$, $\frac{3}{4}$ $V_{BATT}$, ect.)

Constant Current Voltage Limited Operation

Figure 7:
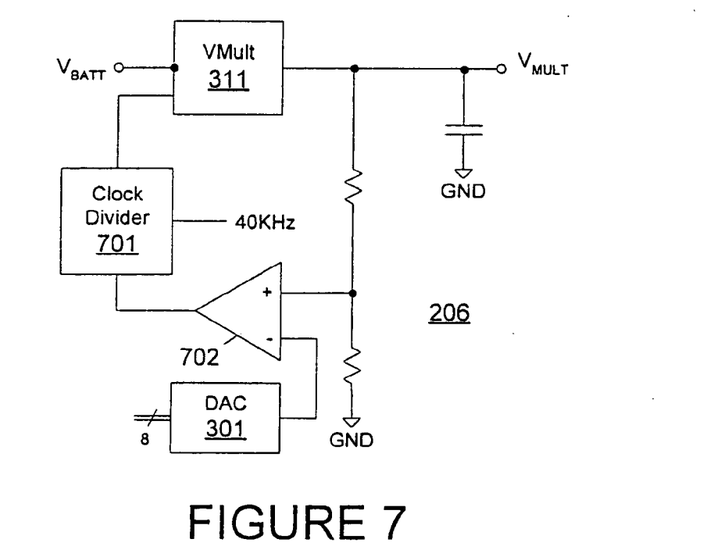
FIG. 7 is a circuit diagram for a constant current voltage limited pulse generator circuit within an output driver for an implantable pulse generator according to one embodiment of the present invention.

In delivery of constant current electrical stimulation pulses, the output of universal custom output driver 206 is optionally voltage limited in the present invention (implemented as a programmable mode). FIG. 7 is a circuit diagram for a constant current voltage limited pulse generator circuit within an output driver for an implantable pulse generator according to one embodiment of the present invention. The voltage-limiting portion of output driver 206 of the illustrated embodiment employs the digital-to-analog converter 301 and the voltage multiplier 311. The clock signal driving voltage multiplier 311 is generated by a clock divider 701 operating on a reference clock signal, such as a 40 kiloHertz (KHz) local oscillator signal.

A comparator 702 compares a voltage-divided value of the output of voltage multiplier 311 to the output of digital-to-analog converter 301. As long as the voltage-divided output of voltage multiplier 311 is less than the output of digital-to-analog converter 301, the clock divider 701 is allowed to run, causing the voltage multiplier to produce more voltage. Once the voltage-divided output of voltage multiplier 311 reaches the output of digital-to-analog converter, however, the clock divider 701 is stopped, causing voltage multiplier 311 to stop producing additional voltage and holding the existing voltage until delivery of a current pulse attenuates that voltage. When the voltage-divided output of voltage multiplier 311 again drops below the output of digital-to-analog converter 301, the clock divider 701 is restarted, together with production of additional voltage by voltage multiplier 311.

Voltage limited operation of constant current pulse delivery by the output driver 206 provides increased safety. If a jump in the resistance of the current sink path occurs (e.g., the patient moves, significantly increasing the resistance between the anode and cathode electrodes selected from electrodes 106–113), the amplitude of the voltage delivered could spike. Limiting the voltage used to drive the current pulse prevents an unsafe jump in the amplitude of the voltage across the electrodes 106–113.

In addition, because the voltage multiplier 311 is not operated continuously, the power consumed by output driver 206 is reduced. Thus, while not helpful for heavy load conditions or high duty cycle and/or fast pulse conditions, constant current voltage limited operation may be employed with less power being consumed and greater patient safety provided.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A system comprising:
a capacitive voltage converter accepting input of a digital control signal for selection of a desired voltage level and outputting said desired voltage level, wherein said desired voltage level is selected from a plurality of voltage levels including non-integer fractional multiples of a supply voltage level used by said capacitive voltage converter; wherein the capacitive voltage converter comprises:
a plurality of capacitors; and
switching circuitry for selectively connecting to the plurality of capacitors, wherein said switching circuitry comprises a plurality of controllable switches, wherein the plurality of controllable switches includes at least a first switch having a higher relative voltage characteristic and a second switch having a lower relative voltage characteristic;
wherein the capacitive voltage converter controls the switching circuitry to generate the desired voltage level according to the digital control signal, wherein the capacitive voltage converter selects between the first and second switches for output switching in relation to a magnitude of the desired voltage level.

2. The system of claim 1 wherein said plurality of controllable switches are partitioned in operation of said capacitive voltage converter to minimize a number of components of said capacitive voltage converter experiencing high voltage levels of said plurality of output voltage levels.

3. The system of claim 1, wherein said plurality of voltage levels include fractional increments comprise ½ increments of said supply voltage level.

4. The system of claim 1, wherein said system comprises:
a therapeutic stimulation pulse generation system.

5. The system of claim 1, wherein said system comprises:
a high power digital to analog converter that provides voltage level output above said source voltage level.

6. A method comprising:
providing a control signal for selecting a desired voltage level from a plurality of voltage levels that include non-integer multiples of a supply voltage level used in generating said desired voltage level; and
switching, under control of said control signal, a plurality of capacitors to generate said desired voltage level;
wherein the switching utilizes a plurality of controllable switches where the plurality of controllable switches includes at least a first switch having a higher relative voltage characteristic and a second switch having a lower relative voltage characteristic;
wherein the switching controls the plurality of switches to generate the desired voltage level according to the control signal by selecting between the first and second switches for output switching in relation to a magnitude of the desired voltage level.

7. The method of claim 6, wherein said switching comprises:
switching a set of high voltage field effect transistors to establish connections between at least some first components used in producing a first range of voltages, and
switching a set of low voltage field effect transistors to establish connections between at least some second components used in producing a second range of voltages lower than the first range.

8. The method of claim 7, wherein said first components and said second components comprise capacitors of said plurality of capacitors.

9. The method of claim 7, wherein said switching further comprises:
stacking a voltage of said first range of voltages and a voltage of said second range of voltages to generate said desired voltage level.

10. The method of claim 6, wherein said switching said plurality of capacitors occurs upon demand for said desired voltage level.

11. The method of claim 6, wherein said control signal is operable to select said desired voltage level from a range of voltage levels including ½ times said supply voltage level through 3 times said supply voltage level.

12. The method of claim 6, further comprising:
providing said desired voltage level to circuitry delivering a therapeutic stimulation pulse to a patient.

13. The method of claim 12, wherein said desired voltage level is used in selecting a current amplitude of said therapeutic stimulation pulse.

14. The method of claim 6, further comprising:
providing a second control signal for selecting a second desired voltage level; and
switching, under control of said second control signal, said plurality of capacitors to generate said second desired voltage level.

15. The method of claim 14, further comprising:
providing one of said desired voltage level and said second desired voltage level to circuitry delivering a therapeutic stimulation pulse to a patient; and
providing the other one of said desired voltage level and said second desired voltage level to circuitry providing an active discharge pulse.

16. A system comprising:
a capacitive voltage converter accepting input of a digital control signal for selection of a desired voltage level and outputting said desired voltage level, wherein said desired voltage level is selected from a plurality of voltage levels including non-integer fractional multiples of a supply voltage level used by said capacitive voltage converter; wherein the capacitive voltage converter comprises:
a plurality of capacitors; and
switching circuitry for selectively connecting to the plurality of capacitors,
wherein said switching circuitry comprises a plurality of controllable switches,
wherein the plurality of controllable switches includes at least a first switch having a higher relative voltage characteristic and a second switch having a lower relative voltage characteristic;
clock conversion circuitry for converting a received clock into respective level-shifted clocks for application to the plurality of controllable switches, wherein the clock conversion circuitry up-shifts the received clock to a maximum level for generation of a level-shifted clock for application to the first switch and, then, down-shifts from the maximum level for generation of a level-shifted clock for application to the second switch.

17. The system of claim 16 wherein the capacitive voltage converter controls the switching circuitry to generate the desired voltage level according to the digital control signal, wherein the capacitive voltage converter selects between the first and second switches for output switching in relation to a magnitude of the desired voltage level.

18. The system of claim 16 wherein the capacitive voltage converter comprises a transmission gate network for passing clock signals from the clock conversion circuitry to the plurality of controllable switches, wherein the transmission gate network comprises field effect transistors (FETs) having different voltage characteristics that are related to the amplitude of the clock signals passing through the respective FETs.

* * * * *